(12) United States Patent
Lee et al.

(10) Patent No.: US 6,673,841 B2
(45) Date of Patent: Jan. 6, 2004

(54) ALPROSTADIL ALKYL ESTER-CONTAINING COMPOSITION FOR EXTERNAL APPLICATION

(75) Inventors: Dong Soo Lee, Kyunggi-do (KR); Kye Kwan Lee, Kyunggi-do (KR); Yun Seok Rhee, Kyunggi-do (KR); Jun Hee Jang, Seoul (KR); Sun Oh Jeoung, Kyunggi-do (KR); Sang Jin Kim, Kyunggi-do (KR); Sang Cheol Chi, Kyunggi-do (KR)

(73) Assignee: Whan In Pharm. Co., Ltd., Seoul (KR)

( * ) Notice: Subject to any disclaimer, the term of this patent is extended or adjusted under 35 U.S.C. 154(b) by 0 days.

(21) Appl. No.: 10/022,254

(22) Filed: Dec. 20, 2001

(65) Prior Publication Data

US 2003/0125382 A1 Jul. 3, 2003

(51) Int. Cl.$^7$ .............................................. A61K 31/557
(52) U.S. Cl. ........................ 514/573; 514/530; 514/946; 514/947
(58) Field of Search ................................ 514/573, 530, 514/946, 947

(56) References Cited

U.S. PATENT DOCUMENTS

| | | |
|---|---|---|
| 5,194,670 A | 3/1993 | Mizushima et al. |
| 5,219,885 A | 6/1993 | Frölich et al. |
| 5,380,760 A | 1/1995 | Wendel et al. |
| 5,681,850 A | 10/1997 | Frölich et al. |
| 5,877,216 A * | 3/1999 | Place et al. ................. 514/573 |
| 5,942,545 A | 8/1999 | Samour et al. |
| 6,306,841 B1 * | 10/2001 | Place et al. ................. 514/149 |
| 6,414,028 B1 * | 7/2002 | Buyuktimkin et al. ...... 514/573 |

FOREIGN PATENT DOCUMENTS

| | | | |
|---|---|---|---|
| KR | 2001-0011625 | | 2/2001 |
| WO | WO00/33825 | * | 5/2000 |

OTHER PUBLICATIONS

Sheu et al., "Investigation of the precutaneous penetration of prostaglandin $E_1$ and its ethyl ester", Journal of Controlled Release, 55, pp. 153–160, 1998.

Yoo, et al., "Stabilization and Permeation Enhancement of $PGE_1$ in a Semi–Solid Topical Preparation", *The 47$^{th}$ Annual Convention of the Pharmaceutical Society of Korea*, 1998.

Ho et al.; "The Percutaneous Penetration of Prostaglandin $E_1$ and its Alkyl Esters"; Journal of Controlled Release, vol. 58, pp. 349–355, (1999).

* cited by examiner

*Primary Examiner*—Vickie Kim
(74) *Attorney, Agent, or Firm*—Finnegan, Henderson, Farabow, Garrett & Dunner LLP

(57) ABSTRACT

The present invention relates to a composition of topical preparation containing alprostadil alkyl ester, and more particularly, comprising an alprostadil alkyl ester, an oily vehicle, a skin permeation enhancer and an anti-irritant agent.

8 Claims, 2 Drawing Sheets

ALPROSTADIL ALKYL ESTER-CONTAINING COMPOSITION FOR EXTERNAL APPLICATION

FIELD OF THE INVENTION

This invention relates to an alprostadil alkyl ester-containing composition for external application.

PRIOR ARTS

Erectile dysfunction refers to a condition of the inability to achieve and maintain penile erection sufficient to complete satisfactory sexual intercourse. There are two major causes for the erectile dysfunction: psychogenic and organic causes. Previously, erectile dysfunction was thought to be of psychogenic origin. In these days, however, it is believed that most of erectile dysfunction comes from organic causes resulting from damage in nerve, blood vessel or hormone system, surgery, or drug administration.

Erectile dysfunction can be cured with surgical or pharmacological means. For the pharmacological treatment, some effective drugs are available, orally or locally. As oral drugs, yohimbine and trazodone have been used, but their clinical effect is not pronounced. Recently, sildenafil, a selective inhibitor of phosphodiesterase, has been introduced into the market as an oral drug. This new oral drug showed positive result in the treatment of erectile dysfunction. However, the oral administration of a drug accompanies systemic side effects inevitably, since the drug reaches the site of action after it is distributed throughout the whole body by the systemic circulation. Sildenafil also has some systemic side effects such as headache, flushing, indigestion and changes in vision, etc. Particularly, it may cause a serious side effect, if taken by patient medicated with organic nitrates, due to the possibility of dramatic drop in blood pressure. Therefore, a local treatment is the method of choice for the treatment of erectile dysfunction, since it is a local disorder. For this purpose, alprostadil (prostaglandin E1), papaverine, or phentolamine has been used. Among them, alprostadil is demonstrated to be the most effective drug for the local treatment of erectile dysfunction. Until now, intracavernous injection and transurethral pellet of alprostadil are commercially available in the market. However, the injection formulation needs a direct injection to the penis. Thus, patients may feel uncomfortable, and a pain or bleeding, or even infection on the injected site may occur. The transurethral pellet also has inconvenience in inserting into urethra, and burning sense on urethra or pain on penis may occur.

As mentioned above, alprostadil shows excellent pharmacological effect in the treatment of erectile dysfunction when applied locally. However, these two invasive methods, intracavernous injection and transurethral delivery, are only available as currently available dosage forms even though a topical preparation is more convenient to apply than those methods. This is due to two problems in the formulation of alprostadil as a topical preparation.

One is the instability of the drug in the conventional topical preparation which usually contains water in it. Like other prostaglandins, alprostadil is degraded easily to prostaglandin $A_1$ or prostaglandin $B_1$ in the presence of water. Examples of patents in relation to topical preparation are U.S. Pat. Nos. 5,194,670 and 5,681,850. However, as mentioned above, topical preparations disclosed in these patents are unstable due to water contained therein.

The other one is that the skin permeation rate of alprostadil itself is too low to achieve therapeutic drug concentration locally when applied topically.

As patents to overcome this problem, in U.S. Pat. No. 6,046,244, alkyl-2-(N,N-disubstituted amino)-alkanoate or (N,N-disubstituted amino)-alkanol alkanoate has been used as the skin permeation enhancer, and in U.S. Pat. No. 5,942,545, dioxolane, dioxane, or acetal. However, these enhancers are not commercially available and there are not sufficient information on the effects of these enhancers other than that as a skin permeation enhancer so far, since these are new materials. The present inventors had found that some pyrrolidones of pharmaceutical or cosmetic grade enhance the skin permeation of alprostadil, and filed a patent application for this invention (Korean Patent Application No. 99-31090). The excellent skin permeation of alprostadil was obtained with the preparation of this patent. Also, the stability of alprostadil in the preparation was highly improved, since the topical formulation in this patent is based on non-aqueous vehicles. However, the preparation in this patent has also a shortcoming of severe topical irritation on the applied area, which may be due to the drug itself or the excipients used or the combination of the two. To overcome this problem, there has been studied for novel preparation containing anti-irritant agent by the inventors. As a result, the inventors have found out a composition which has excellent skin permeation rate with little skin irritation (Korean Patent Application No. 2000-34767).

The rate of skin permeation of alprostadil ethyl ester from the toical preparation in Example 3 were determined using Franz diffusion cell fitted with excised guinea pig skin. A topical preparation containing alprostadil prepared according to Example 3 in Korean Patent Application No. 2000-34767, that is, comparative example 1, was used as a reference. The effective diffusion area was 1.77 $cm^2$. The receptor compartment of the diffusion cell was filled with 0.01 M phosphate buffer (pH 7.4) and its temperature was maintained at 37+0.5° C. and stirred at 600 rpm during the experiment. The amount of alprostadil permeated into the receptor medium was determined with an HPLC method.

Prodrug means a compound that can be chemically transformed during or after absorption through skin, thereby to yield a parent drug, a pharmacologically active compound, via hydrolysis or enzymatic reaction. Generally, prodrug is obtained by transforming physical properties of the drug to enhance membrane permeation rate. A major method to synthesize the prodrug is to convert the drug into a modified form which is easily reactive on esterase which is widely distributed throughout the whole body.

It is reported that carboxyl group of alprostadil can be esterified to form a chain of alkyl group and that when chain length increases, permeation is enhanced by more than 10 times (Ho, H. O. et al. J. Control. Release 1999). Alprostadil alkyl esters having longer alkyl chain length are highly lipophilic and thus are easier to permeate stratum comeum, thereby exhibiting the above effect. And, during skin permeation, the prodrug is decomposed to alprostadil by esterase which is abundant beneath skin.

U.S. Pat. Nos. 5,219,885 and 5,380,760 disclose topical preparation of alprostadil alkyl ester. However, because topical preparation in U.S. Pat. No. 5,219,885 contains water, there is a drawback that alprostadil alkyl ester is easily hydrolyzed in the preparation. On the other hand, because topical preparation in U.S. Pat. No. 5,380,760 is in form of plaster obtained by dispersing drug in pressure sensitive adhesive, it is difficult to apply on the desired site.

SUMMARY OF THE INVENTION

The present inventors discovered a topical preparation containing alprostadil alkyl ester, obtained by dissolving alprostadil alkyl ester as a prodrug into an mixture of oily vehicles, skin permeation enhancers and anti-irritant agents, whose skin permeation is excellent compared to the conventional composition containing alprostadil, thereby to complete the present invention.

Therefore, an object of the present invention is to provide a composition of topical preparation containing alprostadil alkyl ester for the treatment of erectile dysfunction, which has not only excellent skin permeation rate but also is chemically stable.

DETAILED DESCRIPTION OF THE INVENTION

Figure 1:
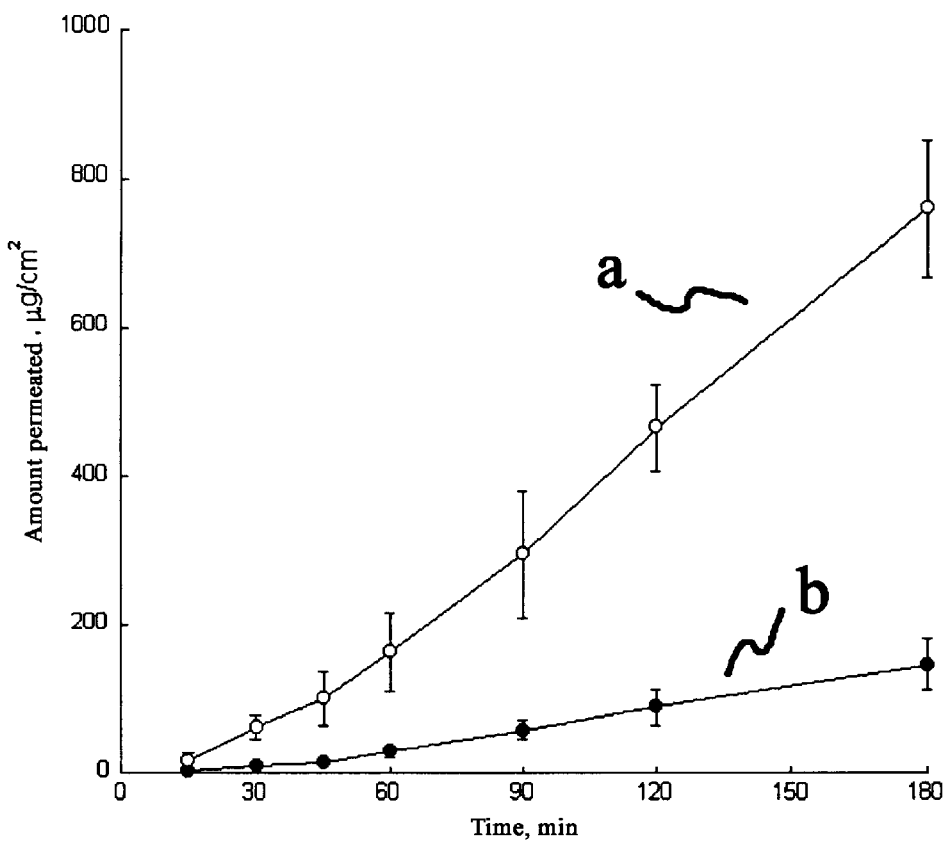
FIG. 1 shows the skin permeation profiles of alprostadil through excised guinea pig skin from a topical preparation containing alprostadil ethyl ester of Example 3 and a topical preparation containing alprostadil of Comparative Example 1 (curve a: Example 3, curve b: Comparative Example 1).

The present invention relates to alprostadil alkyl ester-containing composition for external application. More particularly, the present invention relates to alprostadil alkyl ester-containing composition for external application comprising an alprostadil alkyl ester, an oily vehicle, a skin permeation enhancer and an anti-irritant agent.

As alprostadil alkyl ester according to the present invention, any alprostadil esterified with lower alkyl having 1~5 carbon atoms can be used. Preferably, at least one component selected from the group consisting of alprostadil methyl ester, alprostadil ethyl ester, alprostadil propyl ester, alprostadil isopropyl ester and alprostadil butyl ester can be used.

In the composition of the present invention, alprostadil alkyl ester is preferably present in a range of 0.1~5% by weight, as an amount of alprostadil based on the total weight of the composition. When the amount of alprostadil is less than 0.1 wt %, volume of formulation for application is increased, thereby causing inconvenience, and when the amount of alprostadil is more than 5 wt %, there is drawback that a large amount of drug permeates into skin at once, thereby causing severe skin irritation.

Alprostadil alkyl ester exhibits excellent skin permeation, and alprostadil, an effective ingredient produced by cleavage of ester bond thereof during skin permeation, is provide for inner skin.

Examples of the oily vehicle contained in the composition of the present invention include glycerin esters of fatty acids such as mono- or tri-glycerides of fatty acids, including their polyethylene glycol complex, polyethylene glycol esters of vegetable oils and propylene glycol esters of fatty acids; vegetable oils, including their hydrogenated form, such as sesame oil, soybean oil, castor oil, corn oil, palm oil, peanut oil, cacao oil, cotton seed oil, sunflower seed oil, safflower oil, almond oil and olive oil; fatty acids and their esters, such as oleic acid, linolenic acid, linoleic acid, palmitic acid, palmitoleic acid, arachidonic acid, myristic acid, capric acid, caprylic acid, lauric acid, stearic acid, ethyl oleate, oleyl laurate, isopropyl myristate, isopropyl palmitate, 2-octyldodecyl myristate and cetyl palmitate; and fatty alcohols such as lauryl alcohol, oleyl alcohol, cetyl alcohol and stearyl alcohol. They may be also used as a mixture thereof. The amount of oily vehicle is preferably in the range of 20~80% by weight, based on the total weight of the composition.

Pyrrolidone derivatives are preferred to be employed as skin permeation enhancers to increase the skin permeation of alprostadil alkyl ester, and their examples include: N-methyl-2-pyrrolidone, 2-pyrrolidone, 1-octyl-pyrrolidone, 1-dodecyl-pyrrolidone, 1-caprylpyrrolidone, 1-laurylpyrrolidone, N-ethyl-2-pyrrolidone, N-cyclohexyl-2-pyrrolidone, 1-butyl-3-dodecyl-2-pyrrolidone, 1,5-dimethyl-2-pyrrolidone, 1-hexyl-2-pyrrolidone, 1-hexyl-4-methyloxycarbonyl-2-pyrrolidone, 1-(2-hydroxyethyl) pyrrolidone, 3-hydroxy-N-methyl-2-pyrrolidone, and 1-lauryl-4-methyloxycarbonyl-2-pyrrolidone. They may be also used as a mixture thereof. In the present invention, the amount of skin permeation enhancer is preferably in the range of 5~70% by weight, based on the total weight of the composition. If it is out of this range, it does not exhibit sufficient skin permeation.

Auxiliary skin permeation enhancers may be included into the composition of the present invention in order to further improve the skin permeation of alprostadil alkyl ester. Examples of the auxiliary skin permeation enhancers include non-ionic surfactant such as polyoxyethylene sorbitan fatty acid esters, sorbitan ester and polyoxyethylene alkyl ether. They may be also used as a mixture thereof. The amount of auxiliary skin permeation enhancers is preferably 1~30% by weight, based on the total weight of the composition.

When the topical preparation of alprostadil alkyl ester is applied on the gland, skin irritation may be occurred due to the drug and/or the excipients thereof. The usual symptom is redness on the applied site and in worse case, pain may be accompanied. To reduce these side effects, anti-irritant agents are included. Examples of such anti-irritant agents include squalene, squalane, avocado oil, tocopherol, polyvinyl pyrrolidone, hialulonic acid, aloevera gel, spingosine, betaglucan, rosemary oil and alantoin. They may be also used as a mixture thereof. The amount of the anti-irritant agent in the formulation is preferably in the range of 1~30% by weight, based on the total weight of the composition, depending on the amount of the drug, and also the kind and amount of the excipients used. If less than 1 wt %, it is not sufficient to decrease skin irritation, and if more than 30 wt %, skin permeation of alprostadil alkyl ester may be decreased and even irritation due to the anti-irritant agent used may occur.

Topical preparation containing alprostadil alkyl ester can be prepared by dissolving alprostadil alkyl ester, the effective ingredient, into a mixture of an oily vehicle, a skin permeation enhancer and an anti-irritant agent. The apparent dosage form of the composition of alprostadil alkyl ester prepared as above is liquid. It can be used in itself, or its consistency may be increased for the convenience in carrying or applying. For this purpose, the composition of alprostadil alkyl ester can further include a thickener.

The present invention uses at least one thickener selected from the group consisting of waxes, including their derivatives, such as carnauba wax, white wax, beeswax, cetyl esters, paraffin, vaseline, lanolin and PEG-8 beeswax; metallic salts of stearic acids such as aluminum stearate, calcium stearate, magnesium stearate and zinc stearate; and polyethylene, polyethylene glycol with a molecular weight of 4000–8000, and polyethylene oxide. The amount of the thickener is preferably in the range of 1–50% by weight, based on the total weight of the composition. If it is used more than 50%, the viscosity of the composition becomes too high for proper use.

The following Examples are given with the purpose of giving a better understanding of the object, characteristics, advantages and usefulness of the present invention, but never limit the scope of the present invention.

EXAMPLE 1

| | |
|---|---|
| alprostadil methyl ester | 1.04 |
| isopropyl myristate | 59.96 |
| N-methyl-2-pyrrolidone | 20 |
| oleic acid | 4 |
| avocado oil | 15 |

1.04 g of alprostadil methyl ester (1 g in terms of alprostadil) was added to a mixture of 59.96 g of isopropyl myristate, 20 g of N-methyl-2-pyrrolidone, 4 g of oleic acid and 15 g of avocado oil, and then completely dissolved.

EXAMPLE 2

| | |
|---|---|
| alprostadil ethyl ester | 0.43 |
| octyldodecyl myristate | 29.57 |
| beeswax | 10 |
| N-methyl-2-pyrrolidone | 40 |
| tocopherol | 20 |

After 10 g of beeswax was melted at 70° C., 29.57 g of octyldodecyl myristate is added thereto and mixed completely, then cooled down to room temperature. To this mixture, 40 g of N-methyl-2-pyrrolidone and 20 g of tocopherol were added in order and mixed homogeneously. Then, 0.43 g of alprostadil ethyl ester (0.4 g in terms of alprostadil) was added thereto, and stirred until completely dissolved.

EXAMPLE 3

| | |
|---|---|
| alprostadil ethyl ester | 1.08 |
| propylene glycol caprylate/caprate | 40.92 |
| safflower oil | 5 |
| carnauba wax | 15 |
| N-methyl-2-pyrrolidone | 30 |
| sorbitan oleate | 5 |
| squalene | 3 |

After 15 g of carnauba wax was melted at 70° C., a mixed solution of 40.92 g of propylene glycol caprylate/caprate and 5 g of safflower oil was added thereto and mixed completely, then cooled down to room temperature. To this mixture, 30 g of N-methyl-2-pyrrolidone, 5 g of sorbitan oleate and 3 g of squalene were added in order and mixed homogeneously. Then, 1.08 g (1 g in terms of alprostadil) of alprostadil ethyl ester was added thereto, and stirred until completely dissolved.

EXAMPLE 4

| | |
|---|---|
| alprostadil ethyl ester | 2.16 |
| isopropyl palmitate | 59.84 |
| safflower oil | 10 |
| 1-dodecyl-pyrrolidone | 10 |
| polyoxyethylene 20 sorbitan oleate | 3 |
| squalene | 15 |

To a premixed liquid of 59.84 g of isopropyl palmitate, 10 g of safflower oil, 10 g of 1-dodecyl-pyrrolidone, 3 g of polyoxyethylene 20 sorbitan oleate and 15 g of squalene, was added 2.16 g (2 g in terms of alprostadil) of alprostadil ethyl ester, and stirred until completely dissolved.

EXAMPLE 5

| | |
|---|---|
| alprostadil isopropoyl ester | 0.11 |
| PEG-8 caprylic/capric triglycerides | 19.99 |
| glyceryl stearate | 30 |
| N-methyl-2-pyrrolidone | 15 |
| sorbitan trioleate | 9.9 |
| squalane | 25 |

To a premixed liquid of 19.99 g of PEG-8 caprylic/capric triglycerides, 30 g of glyceryl stearate, 15 g of N-methyl-2-pyrrolidone, 9.9 g of sorbitan trioleate and 25 g of squalane, was added 0.11 g (0.1 g in terms of alprostadil) of alprostadil isopropyl ester, and stirred until completely dissolved.

EXAMPLE 6

| | |
|---|---|
| alprostadil ethyl ester | 1.08 |
| ethyl oleate | 14.92 |
| olive oil PEG-6 ester | 10 |
| N-ethyl-2-pyrrolidone | 40 |
| polyoxyethylene lauryl ether | 30 |
| tocopherol | 4 |

To a premixed liquid of 14.92 g of ethyl oleate, 10 g of olive oil PEG-6 ester, 40 g of N-ethyl-2-pyrrolidone, 30 g of polyoxyethylene lauryl ether and 4 g of tocopherol, was added 1.08 g (1 g in terms of alprostadil) of alprostadil ethyl ester, and stirred until completely dissolved.

Comparative Example 1

| | |
|---|---|
| alprostadil | 1 |
| propylene glycol caprylate/caprate | 41 |
| safflower oil | 5 |
| carnauba wax | 15 |
| N-methyl-2-pyrrolidone | 30 |
| sorbitan monooleate | 5 |
| squalene | 3 |

After 15 g of carnauba wax was melted at 70° C., a mixture of 41 g of propylene glycol caprylate/caprate and 5 g of safflower oil was added thereto and mixed completely, then cooled down to room temperature. To this mixture, 30 g of N-methyl-2-pyrrolidone, 5 g of sorbitan monooleate and 3 g of squalene were added in order and mixed homogeneously. Then, 1 g of alprostadil was added thereto, and stirred until completely dissolved.

Experimental Example 1

As patents to overcome this problem, in U.S. Pat. No. 6,046,244, alkyl-2-(N,N-disubstituted amino)-alkanoate or (N,N-disubstituted amino)-alkanol alkanoate has been used as the skin permeation enhancer, and in U.S. Pat. No. 5,942,545, dioxolane, dioxane, or acetal. However, these enhancers are not commercially available and there are not sufficient information on the effects of these enhancers other than that as a skin permeation enhancer so far, since these are new materials. The present inventors had found that some pyrrolidones of pharmaceutical or cosmetic grade enhance the skin permeation of alprostadil, and filed a patent application for this invention (Korean Patent Application No. 99-31090). The excellent skin permeation of alprostadil was obtained with the preparation of this patent. Also, the stability of alprostadil in the preparation was highly improved, since the topical formulation in this patent is based on non-aqueous vehicles. However, the preparation in this patent has also a shortcoming of severe topical irritation on the applied area, which may be due to the drug itself or the excipients used or the combination of the two. To overcome this problem, there has been studied for novel preparation containing anti-irritant agent by the inventors. As a result, the inventors have found out a composition which has excellent skin permeation rate with little skin irritation (Korean Patent Application No. 2000-34767).

The rate of skin permeation of alprostadil ethyl ester from the toical preparation in Example 3 were determined using Franz diffusion cell fitted with excised guinea pig skin. A topical preparation containing alprostadil prepared according to Example 3 in Korean Patent Application No. 2000-34767, that is, comparative example 1, was used as a reference. The effective diffusion area was 1.77 cm$^2$. The receptor compartment of the diffusion cell was filled with 0.01 M phosphate buffer (pH 7.4) and its temperature was maintained at 37+0.5° C. and stirred at 600 rpm during the experiment. The amount of alprostadil permeated into the receptor medium was determined with an HPLC method.

The permeation profiles of alprostadil from the two different topical preparations are shown in FIG. 1. As shown in FIG. 1, the topical gel of alprostadil ethyl ester prepared according to the present invention resulted in higher skin permeation profile than the comparative example 1. The topical gel prepared according to the present invention resulted in 5 times higher skin permeation rate than the comparative example.

Experimental Example 2

The erectility of living cat was determined, using topical preparation containing alprostadil ethyl ester prepared in Example 3. A topical preparation containing alprostadil prepared according to Example 3 in Korean Patent Application No. 2000-34767 (Comparative example 1) was used as a reference. The cat was anesthetized with pentobarbital and then skin of penis thereof was incised. Then, the incised corpus cavenosum was connected with statum pressure transducer, and the blood pressure was recorded by means of Grass model 7 polygraph. The beginning of erection was determined by the time when inner pressure of corpus cavenosum erection are increased, the extent of erection was determined by maximal length of the penis, and duration of erection was determined by how long the increased inner pressure of corpus cavenous was maintained.

Figure 2:
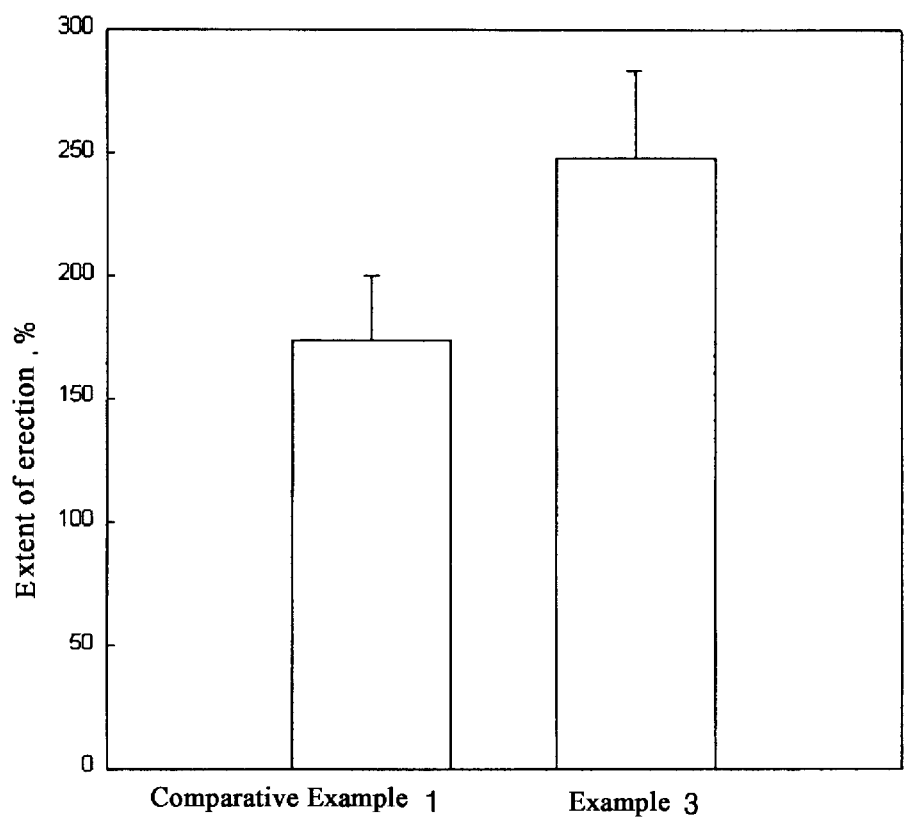
FIG. 2 shows the extent of erection in cat after the applications of a topical preparation containing alprostadil ethyl ester of Example 3 and a topical preparation containing alprostadil of Comparative Example 1.

The extent of erection is shown in FIG. 2. As shown in FIG. 2, the topical preparation containing alprostadil ethyl ester prepared according to the present invention resulted in significantly higher erection profile than the comparative example 1.

The topical preparation containing alprostadil ethyl ester according to the present invention have more excellent effect not only in skin permeation but also in erection than that containing alprostadil.

What we claim is:

1. A topical composition consisting of:
   (i) an alprostadil alkyl ester with alkyl having 1–5 carbon atoms in the range of 0.1–5% by weight;
   (ii) a non-aqueous oily vehicle in the range of 20–80% by weight, which is selected from the group consisting of mono or triglyceride of fatty acids and their polyethylene glycol complex, polyethylene glycol esters of vegetable oils, propylene glycol esters of fatty acids and a mixture of them;
   (iii) a pyrrolidone derivative in the range of 5–70% by weight as a skin permeation enhancer and an auxiliary skin permeation enhancer in the range of 1–30% by weight;
   (iv) an anti-irritant agent in the range of 1–30% by weight and
   (v) a thickener in the range of 1–50% by weight.

2. The composition of claim 1, wherein the alprostadil alkyl ester is at least one selected from the group consisting of alprostadil methyl ester, alprostadil ethyl ester, alprostadil propyl ester, alprostadil isopropyl ester and alprostadil butyl ester.

3. The composition of claim 1, wherein the pyrrolidone derivative is at least one selected from the group consisting of N-methyl-2-pyrrolidone, 2-pyrrolidone, 1-octyl-pyrrolidone, 1-dodecyl-pyrrolidone, 1-capryl pyrrolidone, 1-lauryl pyrrolidone, N-ethyl-2-pyrrolidone, N-cyclohexyl-2-pyrrolidone, 1 -butyl-3-dodecyl-2-pyrrolidone, 1,5-dimethyl-2-pyrrolidone, 1-hexyl-2-pyrrolidone, 1-hexyl-4-methyloxycarbonyl-2-pyrrolidone, 1-(2-hydroxyethyl) pyrrolidone, 3-hydroxy-N-methyl-2-pyrrolidone, and 1-lauryl-4-methyloxycarbonyl-2-pyrrolidone.

4. The composition of claim 1, wherein the anti-irritant agent is at least one selected from the group consisting of squalane, avocado oil, tocopherol, polyvinyl pyrrolidone, hialulonic acid, aloevera gel, spingosine, betaglucan, rosemary oil and alantoin.

5. The composition of claim 1, wherein the auxiliary skin permeation enhancer is non-ionic surfactants.

6. The composition of claim 5, wherein the auxiliary skin permeation enhancer is at least one selected from the group consisting of polyoxyethylene sorbitan fatty acid ester, sorbitan ester and polyoxyethylene alkyl ether.

7. The composition of claim 1, wherein the thickener is at least one selected from the group consisting of waxes and their derivatives, metallic salts of stearic acids, polyethylene, polyethylene glycol with a molecular weight of 4000–8000 and polyethylene oxide.

8. A topical composition consisting of:
   (i) an alprostadil alkyl ester with alkyl having 1–5 carbon atoms in the range of 0.1–5% by weight;
   (ii) a non-aqueous oily vehicle in the range of 20–80% by weight, which is selected from the group consisting of mono or triglyceride of fatty acids and their polyeth ylene glycol complex, polyethylene glycol esters of vegetable oils, propylene glycol esters of fatty acids and a mixture of them;

(iii) a pyrrolidone derivative in the range of 5–70% by weight as a skin permeation enhancer;

(iv) an anti-irritant agent in the range of 1–30% by weight and (v) a thickener in the range of 1–50% by weight.

* * * * *